(12) United States Patent
Liu

(10) Patent No.: US 11,179,528 B2
(45) Date of Patent: Nov. 23, 2021

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 224 days.

(21) Appl. No.: 16/718,137

(22) Filed: Dec. 17, 2019

(65) Prior Publication Data

US 2021/0030980 A1    Feb. 4, 2021

(30) Foreign Application Priority Data

Aug. 2, 2019  (CN) .......................... 201910716305.5
Aug. 2, 2019  (CN) .......................... 201921274653.3

(51) Int. Cl.
*A24F 13/00* (2006.01)
*A61M 15/06* (2006.01)
*A24F 40/46* (2020.01)
*A24F 40/95* (2020.01)

(52) U.S. Cl.
CPC ............. *A61M 15/06* (2013.01); *A24F 40/46* (2020.01); *A24F 40/95* (2020.01); *A61M 2205/8206* (2013.01)

(58) Field of Classification Search
CPC ....................................................... A24F 47/00

USPC ................................................... 131/328–329
See application file for complete search history.

(56) References Cited

U.S. PATENT DOCUMENTS

| 2020/0390153 A1* | 12/2020 | Li  | A24F 40/46 |
| 2021/0045444 A1* | 2/2021  | Liu | A24F 40/44 |
| 2021/0186101 A1* | 6/2021  | Liu | A24F 40/40 |
| 2021/0212369 A1* | 7/2021  | Liu | A24F 40/44 |

\* cited by examiner

*Primary Examiner* — Phuong K Dinh

(74) *Attorney, Agent, or Firm* — Matthias Scholl P.C.; Matthias Scholl

(57) ABSTRACT

An electronic cigarette, including: an atomization assembly and a battery assembly. The atomization assembly is disposed on the battery assembly. The atomization assembly includes a mouthpiece; an atomizer; a first cover; a first silicone seal; a second silicone seal; a stainless iron. The battery assembly includes a third silicone seal; a support frame; an electrode assembly; a light pipe; a first silicone ring; a pneumatic switch; a baffle plate; a battery; a power button; a gasket; a button board; a printed circuit board; a first bracket; a second silicone ring; a vacuum tube; a piece of thermal insulation cotton; a polyimide tube; a heating tube; a second bracket; a housing; a support; a clamp spring; a second cover; a base; and a plurality of ceramic heaters. The first silicone seal is embedded in the first cover. The stainless iron is embedded in the mouthpiece.

1 Claim, 5 Drawing Sheets

ELECTRONIC CIGARETTE

CROSS-REFERENCE TO RELAYED APPLICATIONS

Pursuant to 35 U.S.C. § 119 and the Paris Convention Treaty, this application claims foreign priority to Chinese Patent Application No. 201910716305.5 filed Aug. 2, 2019 and to Chinese Patent Application No. 201921274653.3 filed Aug. 2, 2019. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, Cambridge, Mass. 02142.

BACKGROUND

The disclosure relates to an electronic cigarette.

Conventional electronic cigarettes include an atomization assembly that vaporizes nicotine-containing e-liquid.

SUMMARY

The disclosure provides an electronic cigarette comprising a ceramic heater to combust cigarettes.

The electronic cigarette comprises an atomization assembly and a battery assembly. The atomization assembly is disposed on the battery assembly.

The atomization assembly comprises a mouthpiece; an atomizer; a first cover; a first silicone seal; a second silicone seal; a stainless iron.

The battery assembly comprises a third silicone seal; a support frame; an electrode assembly; a light pipe; a first silicone ring; a pneumatic switch; a baffle plate; a battery; a power button; a gasket; a button board; a printed circuit board; a first bracket; a second silicone ring; a vacuum tube; a piece of thermal insulation cotton; a polyimide tube; a heating tube; a second bracket; a housing; a support; a clamp spring; a second cover; a base; and a plurality of ceramic heaters.

The first silicone seal is embedded in the first cover; the first cover comprises a bottom surface and the second silicone seal is disposed on the bottom surface; one side of the mouthpiece is provided with a cavity and the first cover is disposed in the cavity; the atomizer is disposed in the first cover; and the stainless iron is embedded in the mouthpiece; the electrode assembly is disposed on the support frame; the third silicone seal is sheathed on the support frame; the pneumatic switch is disposed on the printed circuit board; the button board is disposed on the printed circuit board; the printed circuit board is electrically connected to the battery; the first silicone ring is disposed on the pneumatic switch; the first silicone ring and the pneumatic switch are disposed in the support frame; the baffle plate is disposed in the support frame; the heating tube is disposed in the polyimide tube; the polyimide tube is disposed in the piece of thermal insulation cotton; the piece of thermal insulation cotton is disposed in the vacuum tube; the heating tube comprises a plurality of holes, and the plurality of ceramic heaters is embedded in the plurality of holes, respectively; the second silicone ring is sheathed on the first bracket; the first bracket and the second bracket are disposed on two ends of the vacuum tube, respectively; the vacuum tube is disposed in the support frame; and the clamp spring is disposed on the support; the support is embedded in the second bracket; the power button is disposed on the gasket; the gasket is disposed on the button board; the housing is disposed on the support frame; the second cover is disposed between the housing and the base; and the base is directly connected to the housing.

The heating tube comprises a plurality of holes, and a plurality of ceramic heaters are embedded in the plurality of holes. When a cigarette is inserted in the heating tube, press the power button, the ceramic heaters in the heating tube produce heat. Under the temperature of 200-350° C., the cigarette is vaporized by the ceramic heaters. This can reduce the formation of harmful substances during smoking, and the electronic cigarette can consume both the e-liquid and the cigarette.

DETAILED DESCRIPTION

To further illustrate, embodiments detailing an electronic cigarette are described below. It should be noted that the following embodiments are intended to describe and not to limit the disclosure.

Figure 1:
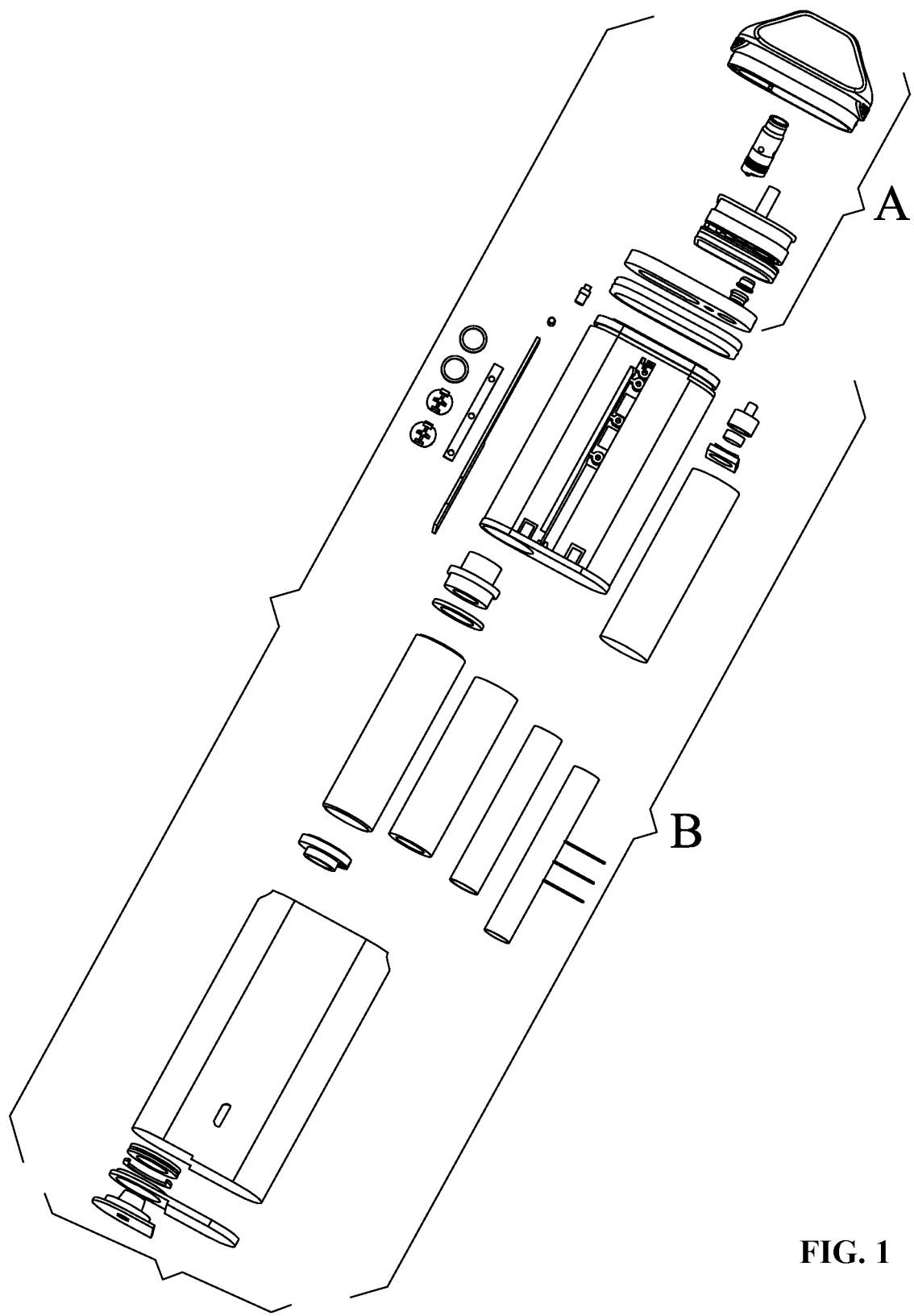
FIG. 1 is an exploded view of an electronic cigarette according to one embodiment of the disclosure.
Figure 2:
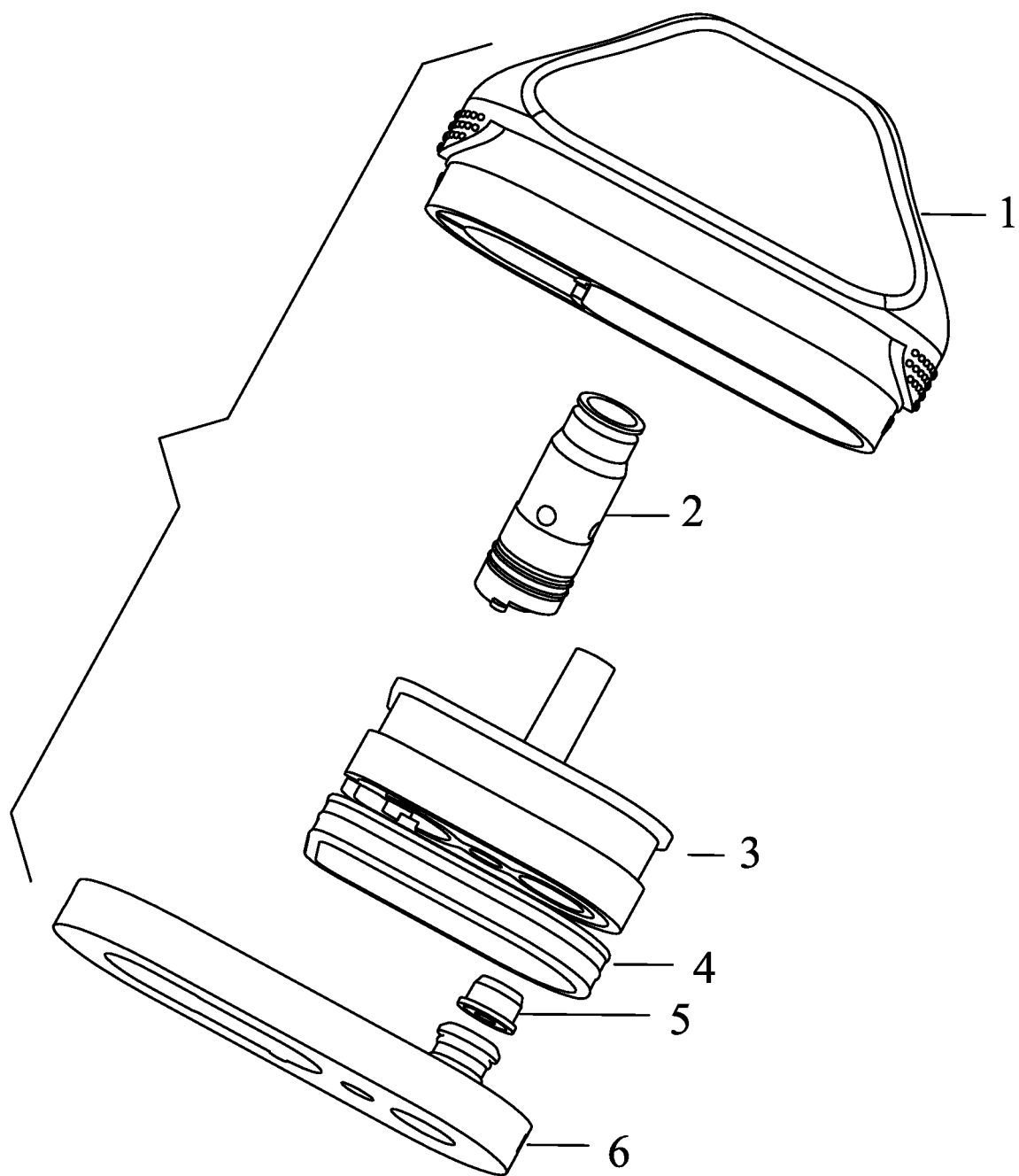
FIG. 2 is an exploded view of an atomization assembly of an electronic cigarette in FIG. 1.
Figure 3:
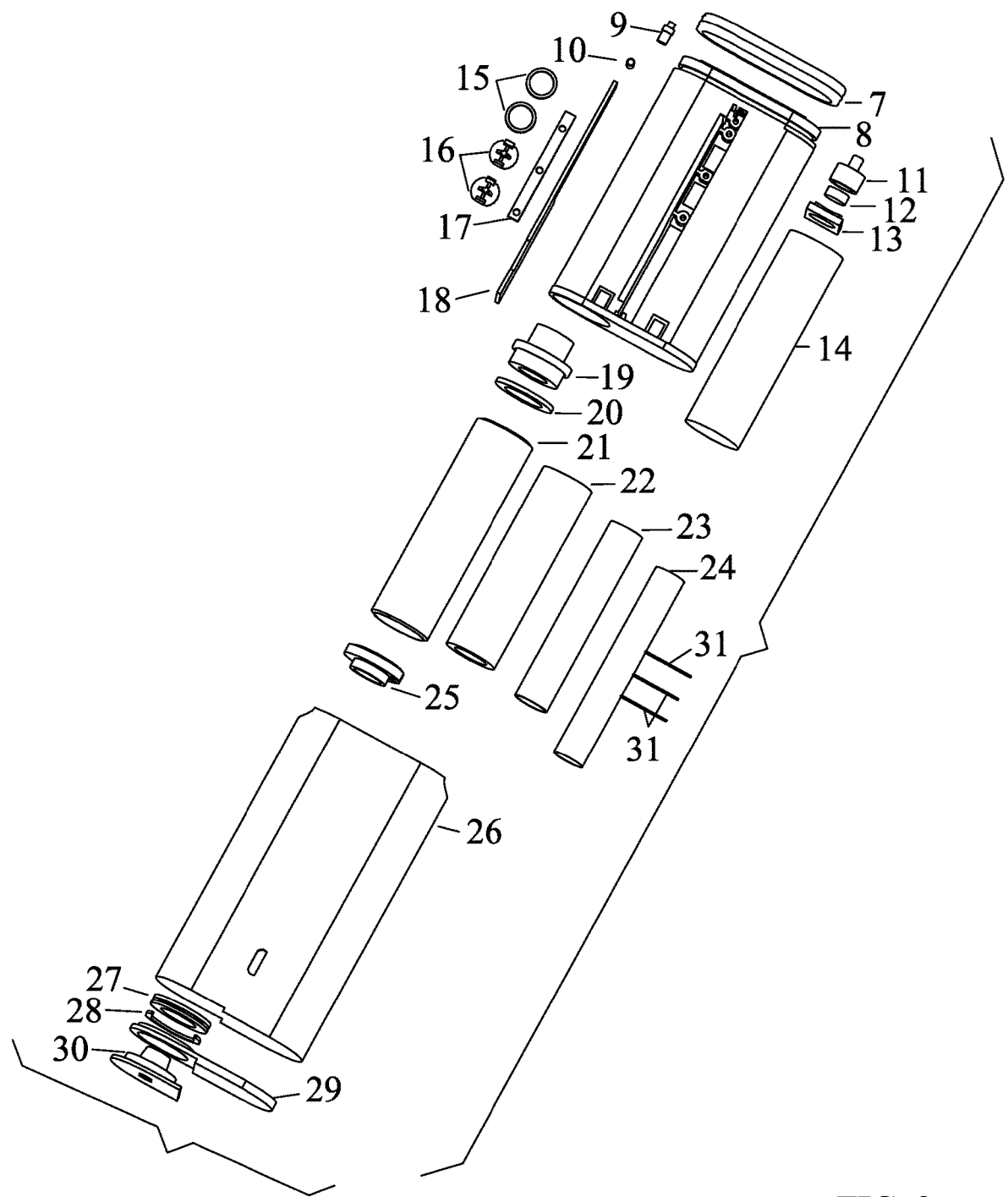
FIG. 3 is an exploded view of a battery assembly of an electronic cigarette in FIG. 1.
Figure 4:
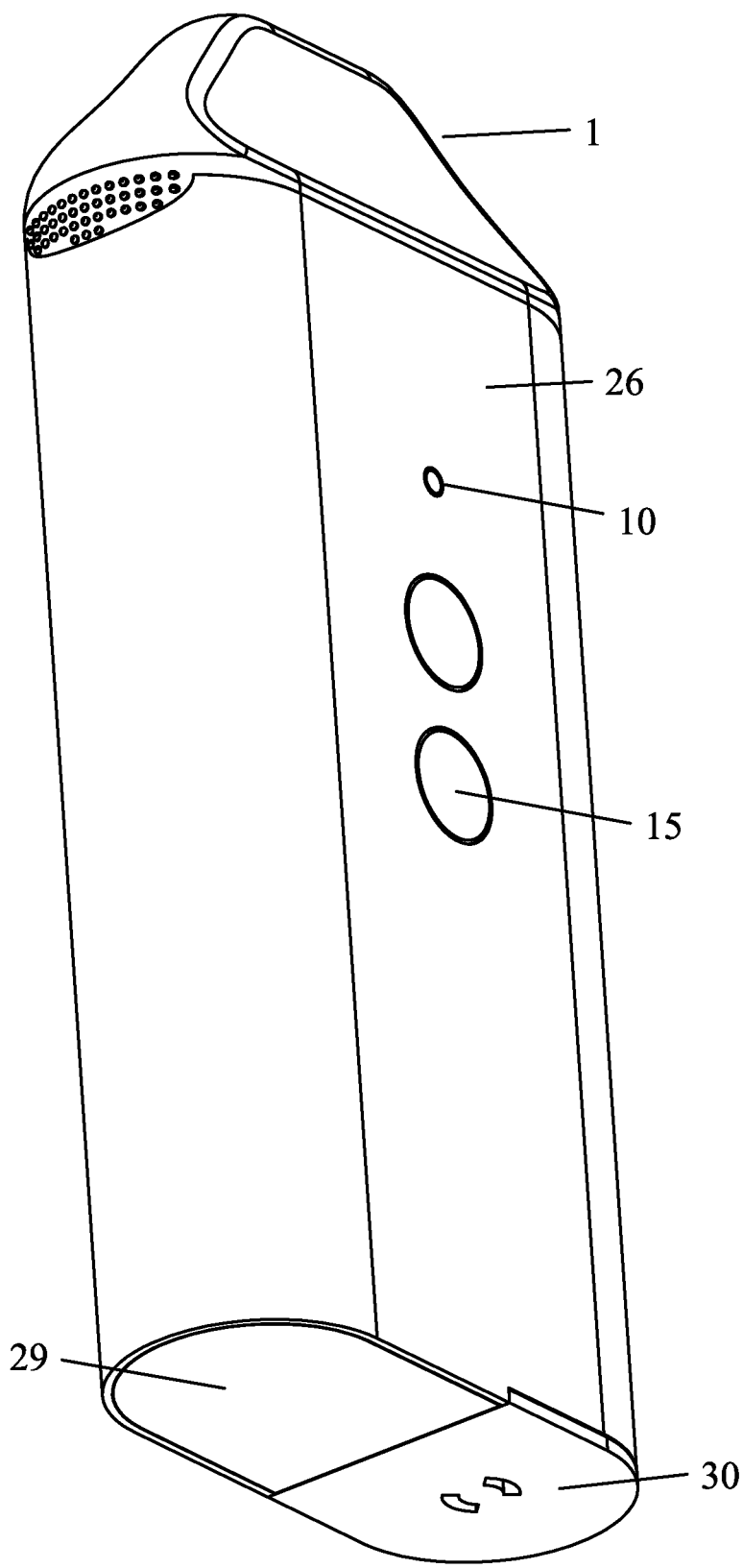
FIG. 4 is a stereogram of an electronic cigarette according to one embodiment of the disclosure.
Figure 5:
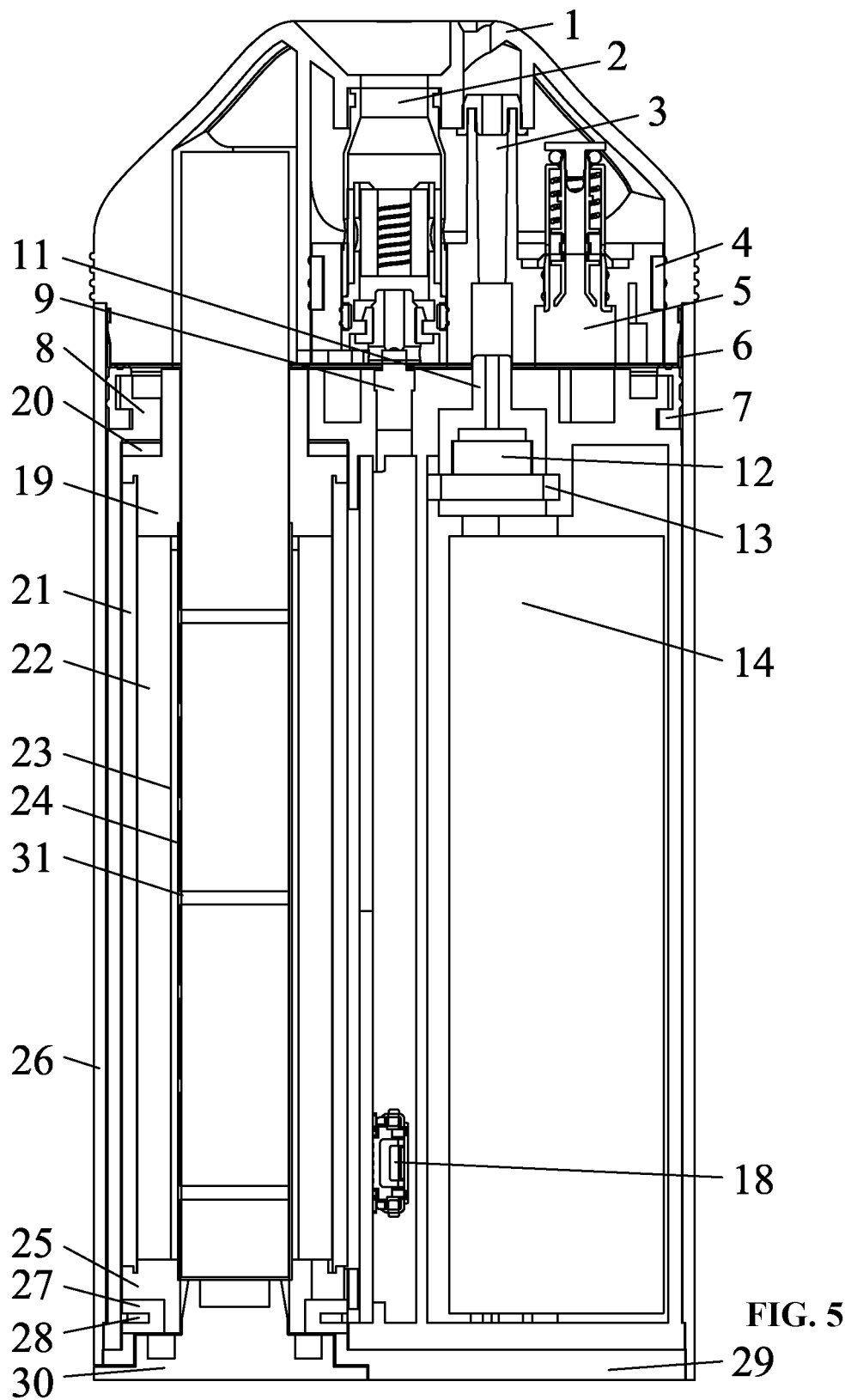
FIG. 5 is a sectional view of an electronic cigarette according to one embodiment of the disclosure.

As shown in FIGS. 1-5, an electronic cigarette comprises an atomization assembly A and a battery assembly B. The atomization assembly A is disposed on the battery assembly B.

The atomization assembly A comprises a mouthpiece 1; an atomizer 2; a first cover 3; a first silicone seal 4; a second silicone seal 5; a stainless iron 6.

The battery assembly comprises: a third silicone seal 7; a support frame 8; an electrode assembly 9; a light pipe 10; a first silicone ring 11; a pneumatic switch 12; a baffle plate 13; a battery 14; a power button 15; a gasket 16; a button board 17; a printed circuit board 18; a first bracket 19; a second silicone ring 20; a vacuum tube 21; a piece of thermal insulation cotton 22; a polyimide tube 23; a heating tube 24; a second bracket 25; a housing 26; a support 27; a clamp spring 28; a second cover 29; a base 30; and a plurality of ceramic heaters 31.

The first silicone seal 4 is embedded in the first cover 3; the first cover 3 comprises a bottom surface and the second silicone seal 5 is disposed on the bottom surface; one side of the mouthpiece 1 is provided with a cavity and the first cover 3 is disposed in the cavity; the atomizer 2 is disposed in the first cover 3; and the stainless iron 6 is embedded in the mouthpiece 1; the electrode assembly 9 is disposed on the support frame 8; the third silicone seal 7 is sheathed on the support frame 8; the pneumatic switch 12 is disposed on the printed circuit board 18; the button board 17 is disposed on the printed circuit board 18; the printed circuit board 18 is electrically connected to the battery 14; the first silicone ring 11 is disposed on the pneumatic switch 12; the first silicone ring 11 and the pneumatic switch 12 are disposed in the support frame 8; the baffle plate 13 is disposed in the support frame 8; the heating tube 24 is disposed in the polyimide tube 23; the polyimide tube 23 is disposed in the piece of thermal insulation cotton 22; the piece of thermal insulation cotton 22 is disposed in the vacuum tube 21; the heating tube 24 comprises a plurality of holes, and the plurality of ceramic heaters 31 is embedded in the plurality of holes, respectively; the second silicone ring 20 is sheathed on the first bracket 19; the first bracket 19 and the second bracket 25 are disposed on two ends of the vacuum tube 21, respectively; the vacuum tube 21 is disposed in the support frame 8; and the clamp spring 28 is disposed on the support 27; the support 27 is embedded in the second bracket 25; the power button 15 is disposed on the gasket 16; the gasket 16 is disposed on the button board 17; the housing 26 is disposed on the support frame 8; the second cover 29 is disposed between the housing 26 and the base 30; and the base is directly connected to the housing 26.

The heating tube 24 comprises three holes, and three ceramic heaters 31 are embedded in the three holes. When a cigarette is inserted in the heating tube 24, press the power button 15, the ceramic heaters 31 in the heating tube 24 produce heat. Under the temperature of 200-350° C., the cigarette is vaporized by the ceramic heaters. This can reduce the formation of harmful substances during smoking, and the electronic cigarette can consume both the e-liquid and the cigarette.

It will be obvious to those skilled in the art that changes and modifications may be made, and therefore, the aim in the appended claims is to cover all such changes and modifications.

What is claimed is:

1. A device, comprising: an atomization assembly and a battery assembly; the atomization assembly comprising:
   1) a mouthpiece;
   2) an atomizer;
   3) a first cover;
   4) a first silicone seal;
   5) a second silicone seal;
   6) a stainless iron;
   the battery assembly comprising:
   7) a third silicone seal;
   8) a support frame;
   9) an electrode assembly;
   10) a light pipe;
   11) a first silicone ring;
   12) a pneumatic switch;
   13) a baffle plate;
   14) a battery;
   15) a power button;
   16) a gasket;
   17) a button board;
   18) a printed circuit board;
   19) a first bracket;
   20) a second silicone ring;
   21) a vacuum tube;
   22) a piece of thermal insulation cotton;
   23) a polyimide tube;
   24) a heating tube;
   25) a second bracket;
   26) a housing;
   27) a support;
   28) a clamp spring;
   29) a second cover;
   30) a base; and
   31) a plurality of ceramic heaters;
   wherein:
   the first silicone seal is embedded in the first cover; the first cover comprises a bottom surface and the second silicone seal is disposed on the bottom surface; one side of the mouthpiece is provided with a cavity and the first cover is disposed in the cavity; the atomizer is disposed in the first cover; and the stainless iron is embedded in the mouthpiece;
   the electrode assembly is disposed on the support frame; the third silicone seal is sheathed on the support frame; the pneumatic switch is disposed on the printed circuit board;
   the button board is disposed on the printed circuit board; the printed circuit board is electrically connected to the battery; the first silicone ring is disposed on the pneumatic switch; the first silicone ring and the pneumatic switch are disposed in the support frame; the baffle plate is disposed in the support frame;
   the heating tube is disposed in the polyimide tube; the polyimide tube is disposed in the piece of thermal insulation cotton; the piece of thermal insulation cotton is disposed in the vacuum tube; the heating tube comprises a plurality of holes, and the plurality of ceramic heaters is embedded in the plurality of holes, respectively;
   the second silicone ring is sheathed on the first bracket; the first bracket and the second bracket are disposed on two ends of the vacuum tube, respectively; the vacuum tube is disposed in the support frame; and
   the clamp spring is disposed on the support; the support is embedded in the second bracket; the power button is disposed on the gasket; the gasket is disposed on the button board; the housing is disposed on the support frame; the second cover is disposed between the housing and the base; and the base is directly connected to the housing.

* * * * *